United States Patent [19]

Harwood et al.

[11] Patent Number: 4,975,281

[45] Date of Patent: Dec. 4, 1990

[54] ANTI-ULCER COMPOSITION

[75] Inventors: Richard J. Harwood, Bensalem, Pa.; Edward V. Henry, Peapack, N.J.; Joseph S. Sonk, Cherry Hill, N.J.; Luke T. H. Foo, Skillman, N.J.; Jay L. Rheingold, Marlboro, N.J.; Robert C. deGroof, Doylestown, Pa.

[73] Assignee: E. R. Squibb & sons, Inc., Princeton, N.J.

[21] Appl. No.: 303,871

[22] Filed: Jan. 30, 1989

[51] Int. Cl.⁵ ............................................. A61K 9/28
[52] U.S. Cl. ................................. 424/441; 514/53; 514/561; 514/566
[58] Field of Search .............. 424/441; 4/690; 514/53, 514/561, 566

[56] References Cited

U.S. PATENT DOCUMENTS

| | | |
|---|---|---|
| 3,432,489 | 3/1969 | Nitta et al. |
| 4,668,665 | 5/1987 | Ishihara et al. ...................... 514/970 |
| 4,676,984 | 6/1987 | Wu et al. ............................... 424/690 |

FOREIGN PATENT DOCUMENTS 0245855  5/1987  European Pat. Off. .

OTHER PUBLICATIONS

Shiau et al., *J. of Pharmaceutical Sciences,* vol. 77, No. 6, pp. 527-530, Jun. 1988.

*Primary Examiner*—Merrell C. Cashion, Jr.
*Assistant Examiner*—P. L. Prater
*Attorney, Agent, or Firm*—Theodore R. Furman, Jr.

[57] ABSTRACT

In accordance with the present invention a novel oral composition and method of using same for the treatment of ulcers and other gastrointestinal disorders is disclosed. The composition comprises an agent capable of forming an ulcer-adherent protective complex in an acid environment combined with one or more alkaline materials in a total amount sufficient to substantially prevent the formation of such a complex in the mouth and adherence of such a complex to the *buccal mucosa.*

24 Claims, No Drawings

ANTI-ULCER COMPOSITION

FIELD OF THE INVENTION

The present invention relates to an improved pharmaceutical composition for anti-ulcer agents, and is particularly concerned with such compositions for anti-ulcer agents which form an ulcer-adherent protective complex in acidic environments.

SUMMARY OF THE INVENTION

In accordance with the present invention a novel oral composition and method of using same for the treatment of ulcers and other gastrointestinal disorders is disclosed. The composition comprises an agent capable of forming an ulcer-adherent protective complex in an acid environment combined with one or more alkaline materials in a total amount sufficient to substantially prevent the formation of such a complex in the mouth and adherence of such a complex to the *buccal mucosa*.

DETAILED DESCRIPTION OF THE INVENTION

The present invention provides an improved composition for ulcer curative/ulcer therapy agents capable of forming an ulcer-adherent protective complex, such as sucralfate. Sucralfate, an aluminum salt of sucrose sulfate ester, is an excellent duodenal ulcer curative agent. Although sucralfate has negligible acid neutralizing capacity, its anti-ulcer activity is apparently the result of the formation of an ulcer-adherent complex that covers the ulcer site and protects it from further attack by acid, pepsin and bile salts. This complex is a gummy, gel-like bioadhesive which forms in acidic environments, e.g., the stomach, and which binds bile salts and inhibits pepsin activity in gastric juices. The complex actually favors adherence to ulcerated or inflamed mucosa.

In a preferred embodiment, the composition of the present invention is in the form of a chewable tablet. The present composition in chewable tablet form is not of a gritty, uncomfortable consistency but rather is of a soft, freely flowing powder when broken up by chewing. This renders the present chewable composition easy to swallow and provides adherence of the preparation to inflammatory sites caused by regurgitational esophagitis, as well as to the duodenal ulcer sites, ulcer sites in the stomach and other ulcer sites. Therefore, the compositions of the present invention, especially the chewable tablet formulation, is useful in the treatment of stomach ulcers, duodenal ulcers, regurgitational esophagitis, hiatal hernia, and symptoms of upset stomach or dyspepsia, e.g., indigestion, "acid stomach", "sour stomach", "full stomach", heartburns, "burning" and the like.

A potential disadvantage with taking an agent such as sucralfate by mouth is premature formation of the gummy complex in the mouth. Although the mouth is generally pH neutral, this premature gumming and adherence of the complex to the *buccal mucosa* can take place when the pH of the mouth is slightly acidic and/or when the mouth is ulcerated. This problem is potentially more prevalent in a chewable formulation. Since sucralfate forms the ulcer-adherent complex in an acidic environment, formulating sucralfate with alkaline materials might be expected to deter the formation of this gummy bioadhesive substance at the ulcer sites to be treated. Surprisingly, however, it has been found that combining such an anti-ulcer agent with one or more alkaline materials can provide a composition which will not prematurely "gum" or "gel" in the mouth, but which still provides highly effective anti-ulcer activity. This is so even with the chewable tablet formulation of the present invention.

The preferred anti-ulcer agent for use with the present invention is sucralfate.

As stated above, the one or more alkaline materials should be present in an amount sufficient to substantially prevent premature formation of the ulcer-adherent complex. A preferred amount for sucralfate compositions has been found to be between about 0.5 and 10 milliequivalents of acid neutralizing capacity. Acid neutralizing capacity as used herein is determined by the "acid neutralizing capacity test" outlined in 21 C.F.R. 331.26. The most preferred amount for the one or more alkaline materials with sucralfate has been found to exist when the range of acid neutralizing capacity is greater than about 0.5 and less than about 5 milliequivalents.

The alkaline materials for use in the present invention can be any convenient pharmaceutically acceptable substances and are preferably selected from the group consisting of magnesium hydroxide, aluminum hydroxide, sodium bicarbonate, magaldrate, calcium carbonate, hydrotalcite, dihydroxy aluminum sodium carbonate, magnesium oxide, magnesium trisilicate and combinations thereof. Most preferred with sucralfate is magnesium hydroxide.

In addition to the anti-ulcer agent and alkaline materials, the composition of the present invention may further comprise one or more ingredients from each of the following categories:

(a) sugars
(b) sweeteners
(c) natural and artificial flavors
(d) flavor enhancers
(e) diluents
(f) diluent/sweetness enhancers
(g) lubricants
(h) preservatives.

For example, in one embodiment the composition of the present invention comprises up to about 30 percent by weight each of one or more diluent/sweetness enhancers provided that the total diluent/sweetness enhancers do not exceed about 60 percent by weight of the composition; up to about 50 percent by weight of one or more sugars; up to about 10 percent by weight of one or more artificial or natural flavors; up to about 5 percent by weight of one or more sweeteners; up to about 5 percent by weight of one or more lubricants; sucralfate and the one or more alkaline materials.

The diluent/sweetness enhancers can be of any such material known in the art, e.g., mannitol, sorbitol, xylitol, aspartame, lycasin, glycerin or ammoniated glycyrhizin.

Likewise, any of the various sugars, flavors, sweeteners, flavor enhancers, diluents and preservatives known in the art of oral pharmaceutical compositions, especially chewable tablets, may be employed.

Similarly any convenient lubricants may be utilized, e.g., magnesium stearate, stearic acid, talc, calcium stearate, sodium stearate, sterotex, sodium stearyl fumarate, stearowet or carbowax.

The compositions of the present invention should contain a pharmaceutically effective amount of the complex forming anti-ulcer agent and may typically include 500 mg to 1 g of an agent such as sucralfate in a tablet form.

A preferred chewable tablet formulation in accordance with the present invention comprises sucralfate; an amount of alkaline materials, e.g., magnesium hydroxide, to provide between about 0.5 and about 5 milliequivalents of acid neutralizing capacity; between about 10 and 20 percent by weight of a first diluent/sweetness enhancer such as sorbitol; between about 10 and 20 percent by weight of a second diluent/sweetness enhancer such as mannitol; between about 20 and 30 percent by weight of sugar; between about 0.1 and 1.5 percent by weight of a flavor; less than about 1 percent by weight of a sweetener (e.g. Magnasweet 165 available from MacAndrews and Forbes Co.); and between about 1 and 2 percent by weight of a lubricant such as magnesium stearate.

The compositions of the present invention, whether is tablets for swallowing whole or chewable tablets, can be prepared as is known in the art. For example, using standard equipment known in the art, the protective complex forming agent and one or more alkaline materials can be blended with a portion, for example 25 percent by weight, of the desired lubricant until uniform. The so-formed mixture can thereafter be compacted to the desired density followed by screening of the so-compacted material. After milling of this material, the sugars, sweeteners, flavors and diluent/sweetness enhancers can be added thereto and blended until a uniform mixture results. Finally, the balance of the lubricant can be blended into the mixture. Tableting can be accomplished using known techniques.

The present invention will now be further described by the following example, however, this invention is not meant to be limited to the details therein.

EXAMPLE

Sucralfate Chewable Tablet

A sucralfate chewable tablet was prepared from the ingredients below using the methodology which follows:

| Ingredient | Mg/Tablet |
| --- | --- |
| Sugar, Baker's Special Crystalline | 338.0 |
| Sucralfate | 500.0 |
| Artificial Creme de Vanilla (flavoring; #11489, Food Materials Corp.) | 2.0 |
| Natural & Artificial Orange Flavor (flavoring; #23330, Food Materials Corp.) | 2.0 |
| Magnasweet 165 (sweetener) | 2.6 |
| Mannitol USP (diluent/sweetness enhancer) | 200.0 |
| Sorbitol NF (diluent/sweetness enhancer) | 200.0 |
| Magnesium Hydroxide USP (alkaline material) (about 1.72 milliequivalents of acid neutralizing capacity) | 50.0 |
| Magnesium Stearate NF (lubricant) | 18.0 |
| | 1312.6 mg |

The sucralfate and magnesium hydroxide were blended with about 25 percent of the total amount of magnesium stearate to be added until a uniform mixture resulted. This blend was compacted, screened and milled. The milled material was thereafter blended with the mannitol, sorbitol, sugar, flavors and magnasweet until uniform. The remainder of the magnesium stearate was screened in and this mixture was again blended until uniform.

The so-formed mixture was thereafter compressed into tablets.

What is claimed is:

1. A pharmaceutical composition comprising a therapeutically effective amount of an agent capable of forming an ulcer-adherent protective complex in an acid environment, and one or more alkaline materials in a total amount sufficient to provide between about 0.5 and 10 milliequivalents of acid neutralizing capacity, whereby formation of said complex in the area of the mouth and adherence of said complex to the *buccal mucosa* are substantially prevented.

2. The pharmaceutical composition of claim 1 wherein said agent is sucralfate.

3. The pharmaceutical composition of claim 1 wherein said alkaline materials are present in an amount sufficient to provide acid neutralizing capacity in the range greater than about 0.5 and less than about 5 milliequivalents.

4. A chewable tablet formulation for an agent capable of forming an ulcer-adherent protective complex in an acid environment, which formulation comprises a therapeutically effective amount of said agent, and one or more alkaline materials in a total amount sufficient to provide between about 0.5 and 10 milliequivalents of acid neutralizing capacity in a pharmaceutically acceptable carrier comprising one or more ingredients selected from sugar, sweeteners, natural and artificial flavors, flavor enhancers, diluents, diluent/sweetness enhancers, lubricants and preservatives.

5. The chewable tablet formulation of claim 4 wherein said agent is sucralfate.

6. The chewable tablet formulation of claim 4 wherein said alkaline materials are present in an amount sufficient to provide about 5 or less milliequivalents of acid neutralizing capacity.

7. The chewable tablet formulation of claim 4 wherein said one or more alkaline materials are selected from magnesium hydroxide, aluminum hydroxide, sodium bicarbonate, magaldrate, calcium carbonate, hydrotalcite, dihydroxy aluminum sodium carbonate, magnesium oxide and magnesium trisilicate.

8. The chewable tablet formulation of claim 4 comprising up to 30 percent by weight each of one or more diluent/sweetness enhancers provided that the total diluent/sweetness enhancers are not more than 60 percent by weight of said formulation; up to 50 percent by weight of one or more sugars; up to about 10 percent by weight of one or more artificial and natural flavors; up to about 5 percent by weight of one or more sweeteners; and, up to about 5 percent by weight of one or more lubricants.

9. The chewable tablet formulation of claim 8 wherein said one or more diluent/sweetness enhancers are selected from mannitol, sorbitol, xylitol, aspartame, lycasin, glycerin and ammoniated glycyrhizin.

10. The chewable tablet formulation of claim 8 wherein said one or more lubricants are selected from magnesium stearate, stearic acid, talc, calcium stearate, sodium stearate, sterotex, sodium stearyl fumarate, stearowet and carbowax.

11. A chewable tablet formulation comprising a therapeutically effective amount of sucralfate; one or more alkaline materials in a total amount sufficient to provide between about 0.5 and 10 milliequivalents of acid neutralizing capacity; between about 10 and 20 percent by weight of sorbitol; between about 10 and 20 percent by weight of mannitol; between about 20 and 30 percent by weight of sugar; between about 0.1 and 1.5 percent by weight of natural and artificial flavors; less than about 1 percent by weight of sweeteners; and between about 1 and 2 percent by weight of lubricants.

12. The chewable tablet formulation of claim 11 wherein said one or more alkaline materials are present in an amount sufficient to provide acid neutralizing capacity in the range greater than about 0.5 and less than about 5 milliequivalents.

13. The chewable tablet formulation of claim 11 wherein said one or more alkaline materials are selected from magnesium hydroxide, aluminum hydroxide, sodium bicarbonate, magaldrate, calcium carbonate, hydrotalcite, dihydroxy aluminum sodium carbonate, magnesium oxide and magnesium trisilicate.

14. The chewable tablet formulation of claim 13 wherein said alkaline material is magnesium hydroxide.

15. In a method for the treatment of stomach ulcers, duodenal ulcers or regurgitational esophagitis, which comprises administering to a patient in need thereof a therapeutically effective amount of an agent capable of forming an ulcer-adherent protective complex;
the improvement comprising combining said agent with one or more alkaline materials in a total amount sufficient to provide between about 0.5 and 10 milliequivalents of acid neutralizing capacity, whereby formation of said complex in the area of the mouth and adherence of said complex to the *buccal mucosa* are substantially prevented.

16. The method of claim 15 wherein said agent is sucralfate.

17. The method of claim 15 wherein said one or more alkaline materials are present in an amount sufficient to provide acid neutralizing capacity in the range greater than about 0.5 and less than about 5 milliequivalents.

18. The method of claim 15 wherein said one or more alkaline materials are selected from magnesium hydroxide, aluminum hydroxide, sodium bicarbonate, magaldrate, calcium carbonate, hydrotalcite, dihydroxy aluminum sodium carbonate, magnesium oxide and magnesium trisilicate.

19. The method of claim 15 wherein said combination of said agent and said one or more alkaline materials is in the form of a chewable tablet further including one or more ingredients selected from sugar, sweeteners, natural and artificial flavors, flavor enhancers, diluents, diluent/sweetness enhancers, lubricants and preservatives.

20. The method of claim 19 wherein, in addition to said agent and said alkaline materials, said chewable tablet comprises up to 30 percent by weight each of one or more diluent/sweetness enhancers provided that the total diluent/sweetness enhancers are not more than 60 percent by weight of said formulation; up to 50 percent by weight of one or more sugars; up to about 10 percent by weight of one or more artificial and natural flavors; up to about 5 percent by weight of one or more sweeteners; and, up to about 5 percent by weight of one or more lubricants.

21. The method of claim 20 wherein said one or more diluent/sweetness enhancers are selected from mannitol, sorbitol, xylitol, aspartame, lycasin, glycerin and ammoniated glycyrhizin.

22. The method of claim 20 wherein said one or more lubricants are selected from magnesium stearate, stearic acid, talc, calcium stearate, sodium stearate, sterotex, sodium stearyl fumarate, starowet and carbowax.

23. A method of treating symptoms of upset stomach or dyspepsia comprising administering to a patient in need thereof a therapeutically effective amount of a chewable tablet formulation of claim 4.

24. A method of treating hiatal hernia comprising administering to a patient in need thereof a therapeutically effective amount of a chewable tablet formulation of claim 4.

* * * * *